United States Patent
Coughlin et al.

(10) Patent No.: US 6,237,418 B1
(45) Date of Patent: May 29, 2001

(54) METHOD AND APPARATUS FOR DETECTING MISAPPLIED CAPS ON CONTAINERS

(75) Inventors: John L. Coughlin, Duxbury; Robert G. Melvin, II, Sandwich, both of MA (US)

(73) Assignee: Benthos, Inc., North Falmouth, MA (US)

( * ) Notice: Subject to any disclaimer, the term of this patent is extended or adjusted under 35 U.S.C. 154(b) by 0 days.

(21) Appl. No.: 09/337,853

(22) Filed: Jun. 21, 1999

(51) Int. Cl.[7] .................... G01H 1/00; G01N 27/20; B07C 5/00
(52) U.S. Cl. ................ 73/579; 73/570; 73/579; 324/226; 324/236; 209/524
(58) Field of Search ................ 73/579, 587, 52, 73/49.3, 592, 602, 598, 45.4; 324/219, 220, 236, 226, 227, 234, 239, 207.26; 209/524

(56) References Cited

U.S. PATENT DOCUMENTS

| | | | |
|---|---|---|---|
| 2,579,404 | 12/1951 | Stevenson | 53/77 |
| 2,689,647 | 9/1954 | Hofstetter et al. | 209/529 |
| 3,301,399 | 1/1967 | Ochs | 209/529 |
| 3,392,829 | 7/1968 | Keinanen | 209/529 |
| 3,469,689 | 9/1969 | O'Neill, Jr. | 209/529 |
| 3,743,853 * | 7/1973 | Dittman et al. | 307/116 |
| 3,802,252 * | 4/1974 | Hayward et al. | 73/52 |
| 4,024,956 | 5/1977 | Cassidy | 209/3.1 |
| 4,313,171 | 1/1982 | Shibasaki | 702/140 |
| 5,195,360 | 3/1993 | Knigge | 73/49.3 |
| 5,353,631 * | 10/1994 | Woringer et al. | 73/52 |
| 5,608,164 | 3/1997 | MacLauchlan | 73/599 |
| 5,861,548 * | 1/1999 | Melvin, II et al. | 73/52 |

* cited by examiner

*Primary Examiner*—Hezron Williams
*Assistant Examiner*—Jacques Saint-Surin
(74) *Attorney, Agent, or Firm*—Francis J. Caufield

(57) ABSTRACT

Method and apparatus by which misshapen crown caps on beverage containers, such as bottles traveling along high-speed bottling lines, may be detected. Bottles are arranged to travel directly beneath a magnetic proximity sensor head placed at a station along a conveyor. A photodetector indicates when a crown cap is properly positioned with respect to the magnetic proximity sensor. In the presence of a crown cap, the sensor head generates a signal having characteristic shapes indicative of properly shaped caps or those that are misshapen. The signal is monitored via algorithms for the presence of the characteristic shapes anticipated for properly shaped and misshapen crown caps and commands are generated in response to detecting reject crown caps. The signal may also be used to detect distorted bottles and to provide height information to a pressure detection station used in conjunction with the crown detector to enhance the rate of detection for poorly sealed bottles having otherwise properly shaped crown caps.

15 Claims, 4 Drawing Sheets

METHOD AND APPARATUS FOR DETECTING MISAPPLIED CAPS ON CONTAINERS

BACKGROUND OF THE INVENTION

This invention relates to a method and apparatus for detecting misapplied caps on containers. More specifically, this invention relates to a method and apparatus which can be used to detect damaged or misapplied crown caps (usually called "bull nose crowns" in the beverage industry) on beverage and other containers.

Beverage containers, for example, are often sealed under internal pressurization (e.g., beer). If biological contamination or seal failure occurs, the beverage quality may be significantly degraded and may be dangerous to consumers. Even if not resulting in a health hazard, improperly applied caps create the perception of poor quality and can result in lost sales for cosmetic reasons. Accordingly, some manufacturers test the internal pressure/vacuum of containers before shipment to identify and remove defective containers.

Two non-intrusive testing techniques are shown in Hayward, U.S. Pat. No. 3,802,252 and Woringer, U.S. Pat. No. 5,353,631, both of which are assigned to Benthos, Inc., and incorporated herein by reference. Systems of the type described in the foregoing patents have been sold under the name TapTone®. In such systems, a conductive surface of a closed container is vibrated without contacting it. This is accomplished using a pulsed magnetic field, and the resulting sound is analyzed to determine the pressure in the container. A microphone senses the resulting acoustic energy and converts it into an electrical signal. In the Hayward scheme, analog electronics are used to determine whether the signal has prescribed levels of energy within a pre-tuned frequency band. If a signal is detected within the band, it is inferred that the can is good. In the Woringer scheme, a similar test is performed using digital signal processing (DSP) electronics and software. Bottles displaying abnormal characteristics are ejected from the production line.

U.S. Pat. No. 5,861,548 issued on Jan. 19, 1999 and assigned to the same assignee as the present application, describes a further development on the aforementioned Woringer scheme; the entire disclosure of this patent is herein incorporated by reference. As discussed in '548 patent, closed containers are complex vibratory systems which often exhibit nonlinear effects, and it is not uncommon to find in the use of such systems that the acoustic return signals have been modulated by vibratory modes other than the fundamental mode of the container typically used to predict internal pressure. When such distortions are present, the acoustic signal has been corrupted by misleading information that can lead to false rejections of containers. Accordingly, this patent describes a method in which the original information derived from the detected sound is tested to determine whether a modulating distortion is present therein. If such a modulating distortion is found, its effects are compensated, thereby producing demodulated information. If no modulating distortion is detected, the testing steps of the method (which involve determining whether frequency and amplitude components of the information derived from the detected sound satisfy predetermined spectral frequency and amplitude conditions) are carried out on the original information. If, however, a modulating distortion is detected, the testing steps are carried out on the demodulated information.

The methods and apparatus described in the aforementioned patents have been eminently successful in measuring the pressure of closed containers such as beer bottles traveling at commercial production line speeds, for example, of 1000 bottles per minute or more. However, a serious problem has arisen from the aforementioned misaligned or bull nose crown caps.

Crown caps are installed on-line by high speed capping machines, and when properly applied, should look as shown in FIG. 1 of the accompanying drawings. As shown there, the crown cap (generally designated 10) is applied to a bottle 12 having circular symmetry (e.g., a typical commercial beer bottle), the bottle having at its upper end an essentially cylindrical neck portion 14 having walls defining a circular aperture (not visible in FIG. 1), which is closed by the crown cap 10. The cap 10 has a central circular portion 16, which closes the aperture in the bottle. A skirt 18 may extend outwardly and downwardly from the periphery of the circular portion 16. A plurality of crimped portions 20 are formed in the skirt 18 and serve to grip the neck portion 14, thus securing the cap 10 to the neck portion 14 and sealing the bottle 12. Alternatively, a crown may be applied by twisting on to a bottle, engaging thread on an upper surface.

FIG. 2 shows a misapplied, bull nose crown cap 10'. Essentially, a bull nose crown cap arises when the capping machine displaces the center of the cap from the axis of the bottle, or the cap slides across the neck portion of the bottle during its application. In either case, the end result is that on one side of the cap 10' a portion 22 of the skirt 18' descends lower than usual, while on the opposed side of the cap 10' a portion 24 of the skirt 18' does not extend beyond the periphery of the neck portion 14 of the bottle 12. A bull nose crown may also be a dented crown.

A bull nose cap does not make a gas-tight seal to the bottle and hence the bottle leaks and usually has no internal pressure and should thus be rejected from the bottling line. However, automated detection of bull nose caps is surprisingly difficult. Because of the force applied by commercial high speed capping machines, the central portion of a bull nose cap such as that shown in FIG. 2 is essentially flat and at the same height as the correctly applied cap shown in FIG. 1. Accordingly, a bull nose cap cannot be detected simply by measuring the height of the cap with a photodetector. Also, surprisingly, often bull nose caps, when vibrated by the aforementioned Hayward or Woringer apparatus, emit at essentially the same frequency as a properly installed cap, as shown in FIG. 1. Thus, bull nose caps are a plague to customers and bottlers alike, and it is highly desirable to provide some method for detecting such caps on bottling lines. Accordingly, it is a primary object of the present invention to provide such a method and an apparatus for carrying out this method.

Other objects of the invention will, in part, be obvious and will, in part, appear hereinafter when the following detailed description is read in conjunction with the drawings.

SUMMARY OF THE INVENTION

Accordingly, this invention provides a method for detecting an improperly applied crown cap on a container, the method comprising: passing the container bearing the crown cap past a magnetic proximity sensor; deriving from the sensor a signal representative of the position of the crown cap on the container; and analyzing this signal to determine whether the signal does or does not correspond to the form of the signal expected from a correctly applied crown cap.

This invention also provides apparatus for detecting an improperly applied crown cap on a container, this apparatus comprising: a magnetic proximity sensor; transport means for moving the container bearing the cap past the magnetic proximity sensor; means for deriving from the sensor a signal representative of the position of the crown cap on the container; and means for analyzing this signal to determine whether the signal does or does not correspond to the form of the signal expected from a correctly applied crown cap.

BRIEF DESCRIPTION OF THE DRAWINGS

The structure, operation, and methodology of the invention, together with other objects and advantages thereof, may best be understood by reading the detailed description in conjunction with the drawings in which each part has an assigned numeral that identifies it wherever it appears in the various drawings and wherein.

DETAILED DESCRIPTION

Figure 3:
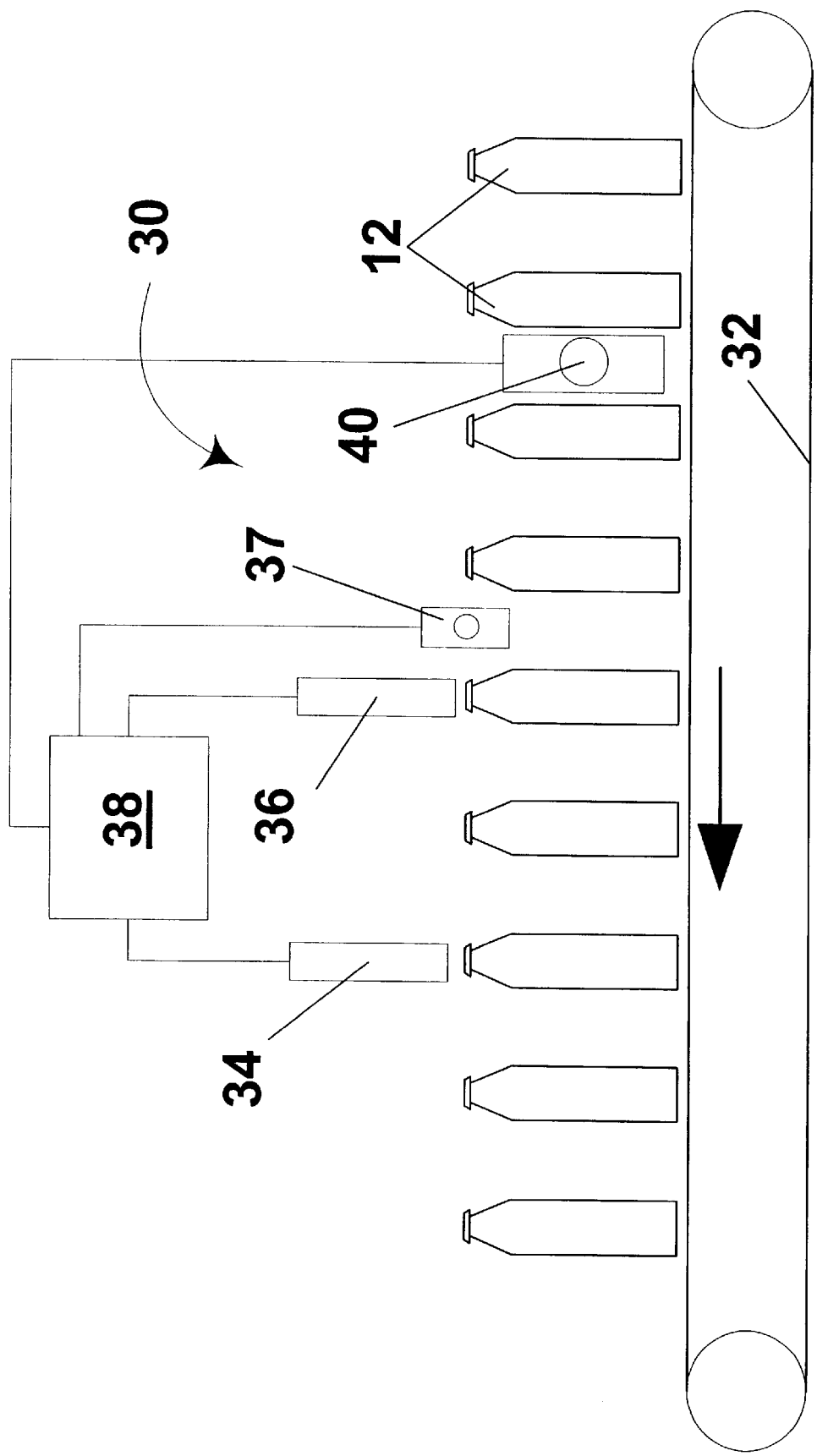
FIG. 3 is a schematic side elevation of a preferred apparatus of the invention.

A preferred embodiment of the invention will now be described, though by way of illustration only. FIG. 3 of the accompanying drawings shows schematically an apparatus as described in the aforementioned U.S. Pat. No. 5,861,548, which has been modified so that it also carries out the method of the present invention. The apparatus (generally designated 30) shown in FIG. 3 comprises a transport means in the form of a conveyor belt 32 which moves a series of bottles 12, which have already been capped with crown caps 10, in one direction, namely from right to left in FIG. 3. Positioned above the conveyor belt 32 are an "acoustic" head 34 as described in the aforementioned U.S. Pat. No. 5,861,548, and, "upstream" from this acoustic head 34, a magnetic proximity sensor head 36. Just forward of head 36 is a photoelectric cap detector 37 for determining the presence of the leading edge of a cap with respect to its position beneath magnetic proximity sensor head 36 and generating a signal to data processing unit 38 to alert it to begin acquiring data from magnetic proximity sensor head 36 at an appropriate sampling rate which may be determined in a well-known manner. Both heads 34 and 36 are also preferably electronically linked to a common data processing unit 38 but not necessarily. While cap detector 37 is preferred because it slightly improves the rejection detection rate, it is not essential since data acquisition may be triggered directly from the signal generated by magnetic proximity sensor head 36 by turning on the data acquisition function when the signal level exceeds a predetermined threshold value that may be adjusted as needed by the requirements of a particular line and bottle parameters. It will be appreciated in this connection, that the absence of a cap altogether provides a null signal and thus a basis for rejecting a bottle as having no cap.

A bottle rejection device 40 is disposed downstream from the head 34 and linked to the data processing unit 38 so that, upon the unit 38 generating a signal indicating that a specific bottle 12 should be rejected, the rejection device 40 pushes the relevant bottle off the conveyor belt 32 into a rejected bottles hopper (not shown).

The acoustic head 34 functions in the same manner as described in the aforementioned U.S. Pat. No. 5,861,548. Thus, as each bottle 12 passes beneath the head 34, this head induces vibration in the cap 10, detects sound resulting from this vibration, and derives information in the form of an electrical signal representing the detected sound, this signal being passed to the data processing unit 38. The unit 38 determines whether a frequency component of the signal corresponds to a predetermined spectral frequency and whether an amplitude component of the signal corresponds to a predetermined amplitude condition. As described in the aforementioned '548 Patent, the unit 38 also tests the signal from the acoustic head 34 to determine whether a modulating distortion is present therein, and if so, compensates for the effects of this modulating distortion, thereby producing a demodulated signal. If the unit 38 determines that such a modulating distortion is present, the aforementioned testing of the frequency and amplitude components of the signal is carried out on the demodulated signal; however, if the unit 38 does not detect any modulating distortion, this testing is carried out on the original signal from the acoustic head 34.

While the center lines of magnetic proximity sensor head 36 and bottles 12 are substantially aligned, it may be desirable to offset them to accentuate any asymmetries in the position of a cap 10 with respect to a bottle 12. Although not shown, such an offset would be such that the center line of the conveyor belt 32 and that of the head 36 were purposely misaligned causing a bottle cap not to pass directly over the central axis beneath the head 36. A slightly offset head may detect bull nose caps more readily than a head disposed exactly above the axes of the bottles since the offset head could cause the output signal to vary with the azimuth of the bottle (i.e., with the angle of the bull nose cap relative to the long axis of the conveyor belt 32) but will always be different from that of a properly capped bottle.

Figure 4:
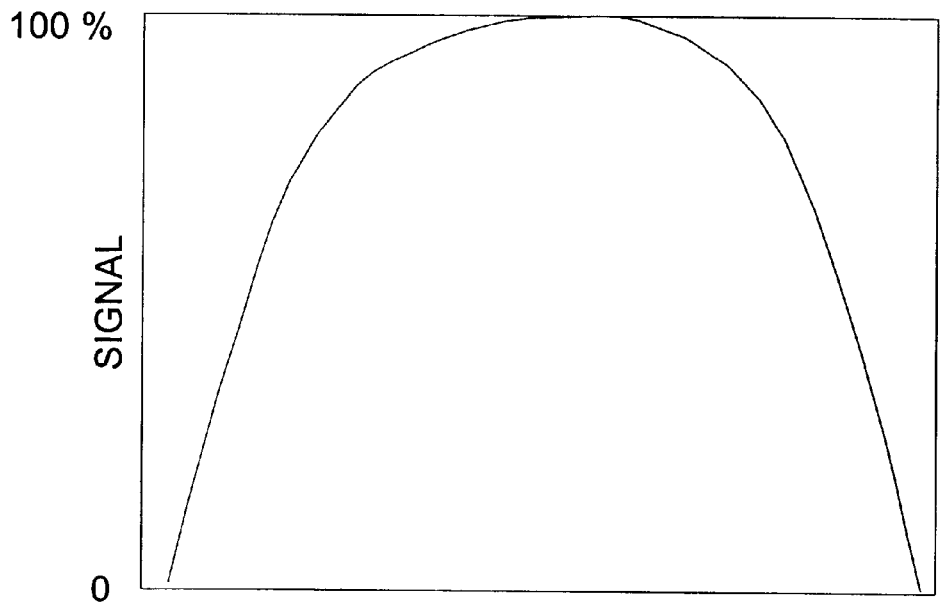
FIG. 4 shows a typical output from the apparatus shown in FIG. 3 as a properly capped bottle passes the apparatus.

The magnetic proximity sensor head 36 generates a signal which is fed to the unit 38. The signal from the head 36 essentially measures the contour of the crown cap. A typical plot of signal against time (which, as the bottles move past the head 36 at a uniform speed is a plot of signal against bottle position) for a correctly capped bottle is shown in FIG. 4. As will be apparent from this Figure, the correctly capped bottle produces a signal which has substantially the form of a parabola, vertex upwards, the signal increasing monotonically from zero to its maximum and then decreasing monotonically back to zero. The signal has only a single maximum.

Figure 5:
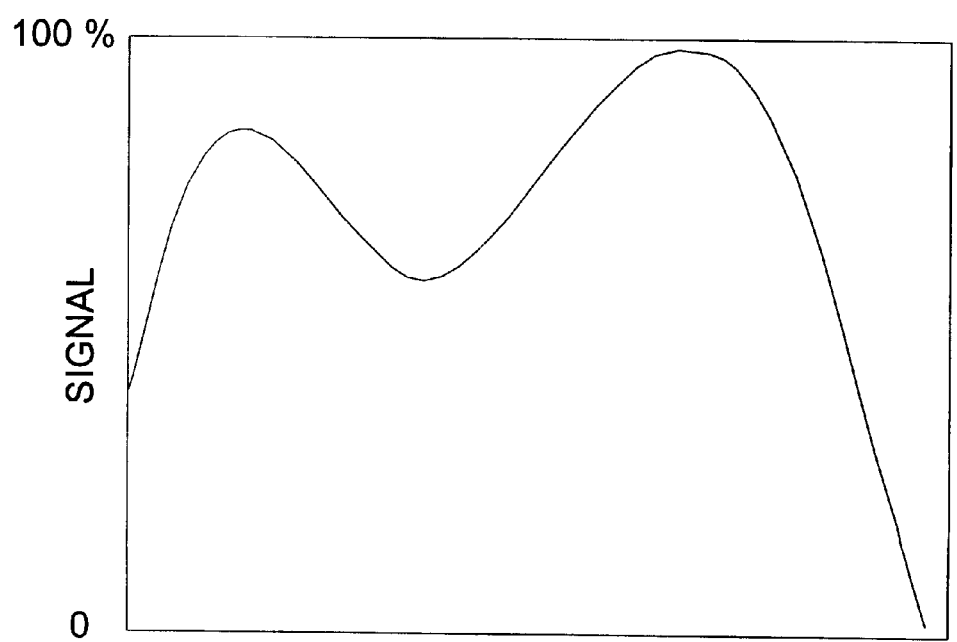
FIG. 5 shows a typical output from the apparatus shown in FIG. 3 as a bottle bearing a bull nose crown cap passes the apparatus.

In contrast, FIG. 5 shows the plot for a bull nose capped bottle. It will be immediately apparent that the overall form of the plot in FIG. 5 is very different from that in FIG. 4, the bull nose cap typically generating a signal with two widely separated maxima separated by an intervening minima. Those skilled in the art of automated data processing will recognize that there are a number of techniques for distinguishing between the "one-maximum" curve of FIG. 4 and the "two-maxima" curve of FIG. 5 which can be programmed into the unit 38 to distinguish between outputs indicative of properly capped and bull nose capped bottles is well within the level of skill in the art.

Two preferred algorithms that have been found successful for distinguishing between properly capped and bull nose capped bottles comprise the "symmetry" test and the "dimple" test. Preferably, if a crown fails either one of these tests, it is rejected. With the "symmetry" test, the 50% signal level is first established by taking dividing the peak signal value in half. The area under the leading edge of the signal curve is then determined by integrating from the time a cap is first detected beneath sensor head 36 till the 50% signal level is reached to determine a first integrated area. A second integrated area is also determined by integrating the area under the trailing edge of the signal from the 50% point to where the signal drops to a value corresponding substantially to its initial value. If the ratio of the areas as set forth in the following equation is not satisfied, then a bottle is rejected:

$$\frac{A_1}{A_2} > k \quad (1)$$

where $A_1$ is the smaller of the two areas, $A_2$ is the larger, and k is a parameter whose value can be adjusted to achieve varying levels of detection sensitivity. A value of k that has been found satisfactory is about 0.75, but this can be adjusted as needed to suit the circumstances of a particular line and bottle and cap parameters.

The "dimple" test is conducted In accordance with the following equation:

$$\frac{Max_1 + Max_2}{Min_{int}} < q, \quad (2)$$

where the maxima are summed and divided by the intervening minimum signal level, and q is a parameter whose value may be adjusted as needed to achieve varying levels of detection sensitivity. A value of q that has been found satisfactory is about 0.35, but this may be changed as required by particular line and bottle details.

Other algorithms are possible. For example, the number of "zero" crossings may be counted by monitoring the slope of the signal. It is clear from observation that there is only one zero slope in FIG. 4 while in FIG. 5 there are three. Consequently, the test here is for the presence of either one or three "zero" crossings, and such an algorithm may be easily implemented via suitable code.

Figure 1:
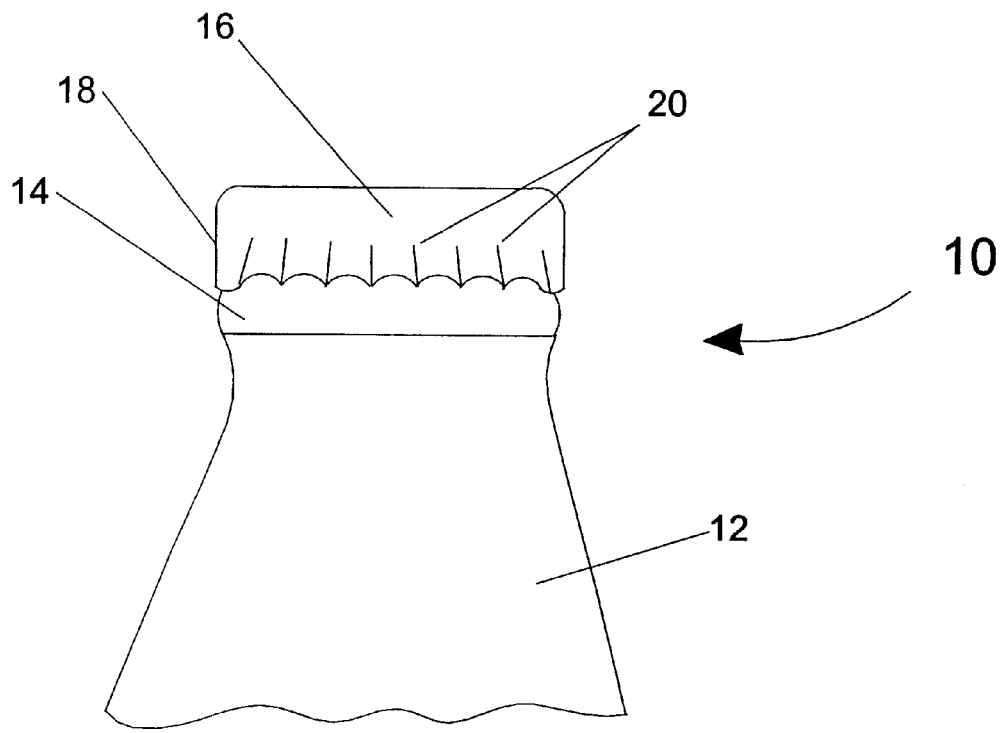
FIG. 1, as already noted, shows a crown cap correctly applied to a bottle.
Figure 2:
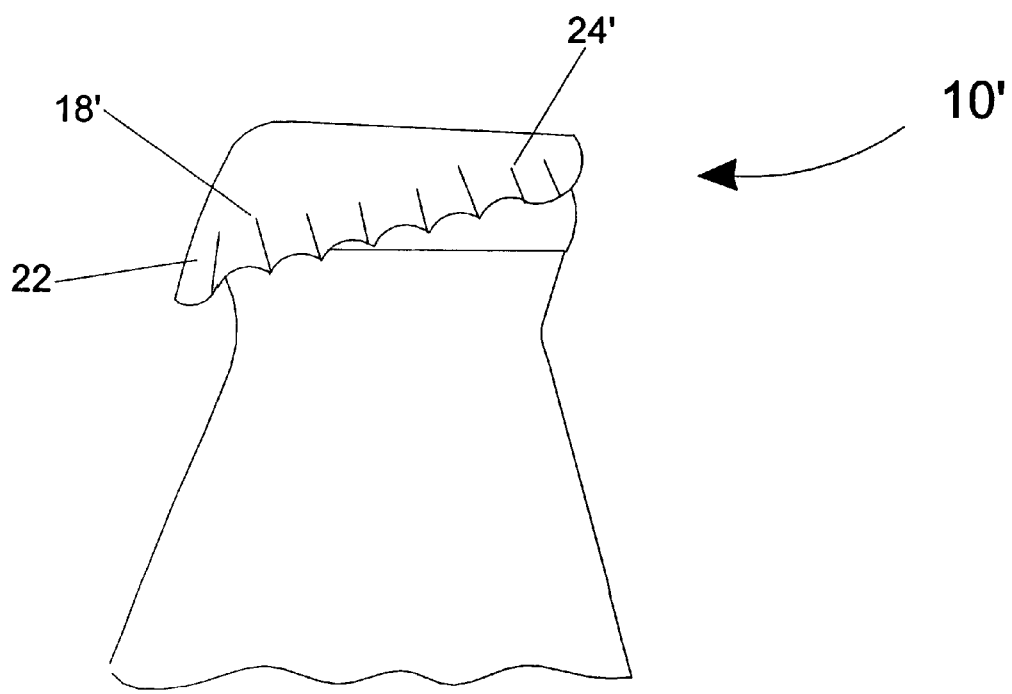
FIG. 2, also as already noted, shows a bull nose crown cap on a bottle.

Another approach is simply to count the number of maxima. In FIG. 4 there is one and in FIG. 2 there are two. Hence, the distinction between good and reject caps may be made on the basis of whether or not there are one or two maxima in the signal.

Figure 6:
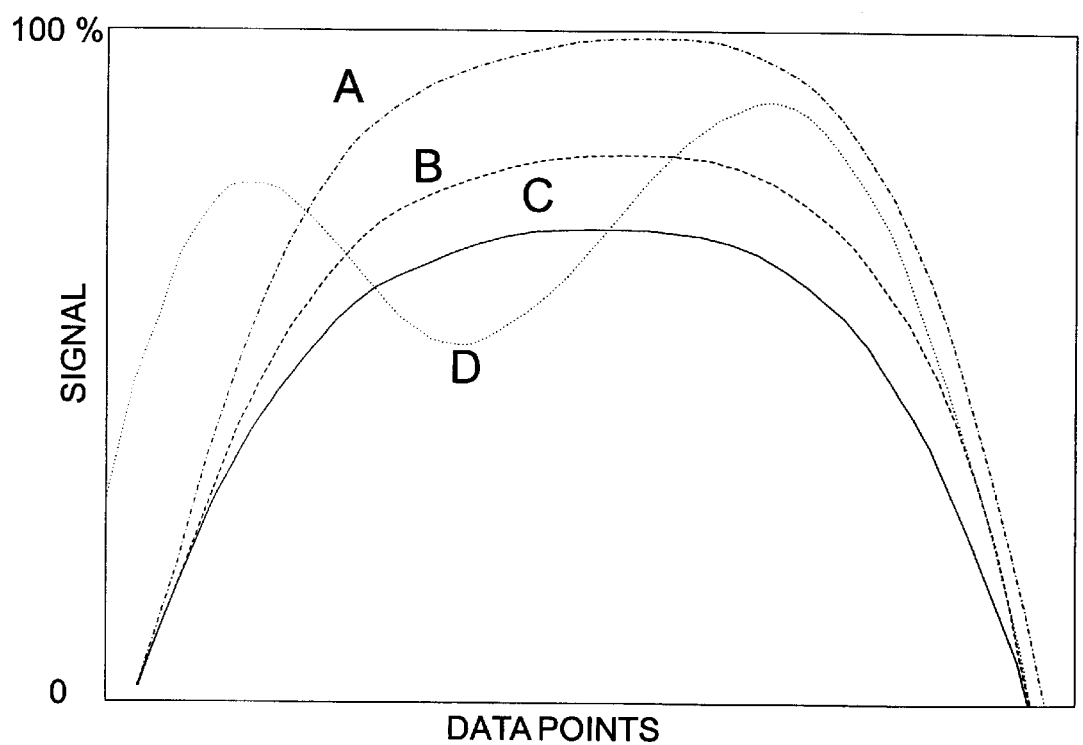
FIG. 6 shows outputs, similar to those shown in FIGS. 4 and 5, of three properly capped bottles of differing heights and one bottle bearing a bull nose crown cap.

Experimentally, it has been found that, although the absolute values of the signals from the head 36 will vary with the height of the cap above the conveyor belt 32 (as would be expected, since the magnetic proximity sensor essentially measures the distance between the sensor and the cap), the general shape of the signal versus time graph remains substantially unchanged by variations in this height. This is illustrated in FIG. 6, which shows plots similar to those shown in FIGS. 4 and 5. In FIG. 6, curves A, B and C are derived from three properly capped bottles; curve A being derived from the tallest bottle and curve C from the shortest. Curve D is derived from a single bull nose capped bottle. From FIG. 6, it will be seen that, although the values of the maxima vary, curves A, B and C all have a single central maximum, while curve D from the bull nose capped bottle has the characteristic two-maxima form shown in FIG. 5. Thus, the ability of the apparatus shown in FIG. 3 to distinguish between properly capped and bull nose capped bottles is essentially unaffected by changes in bottle height within the limits encountered on a conventional bottling line.

However, FIG. 6 also shows that the signal from the head 36 can be used to measure the bottle height with considerable accuracy, since once the apparatus has determined that the curve has the correct single-maximum form for a properly capped bottle, the value of this maximum measures the height of the bottle. The output from the acoustic head 34 also varies with bottle height, since both the amplitude of the vibration induced in the bottle by a given output from the head 34, and the level of sound detected by the head from a specific level of vibration in the bottle, are affected by the distance between the head 34 and the bottle 12, and thus by the height of the bottle. However, there is no easy way to measure the height of the bottle directly from the signal from the head 34. Thus, the limits set for the testing of the amplitude component of the signal from the head 34 must be wide enough to encompass results from bottles having a range of heights, and accordingly some bottles which should possibly be rejected may slip through. However, by feeding both the signals from the heads 34 and 36 to the common data processing unit 38, this data processing unit can first calculate the height of the bottle, using the signal from head 36 as described above, and then appropriately adjust the limits for the testing of the amplitude and/or frequency components of the signal from the head 34 to allow for the bottle height thus calculated, thus improving the accuracy of the acoustic testing.

It has also been observed that optimal results are obtained when conveyor 32 is adjusted so that the vertical axes of bottles 12 are substantially perpendicular to it thus making the central axis of a bottle and that of magnetic sensor head 36 substantially parallel. Put another way, if X represents the direction of travel of a bottle along conveyor 32, then there should be substantially little yaw angle of the vertical axis of a bottle with respect to the X. While, the yaw angle should be as small as possible, it should preferably be less than from about 3–5 degrees. An added benefit to keeping the yaw angle small is that it is possible with the invention to detect poorly shaped or distorted bottles since misshapen bottles will manifest themselves as the equivalent to bull nose crowns.

It will be apparent to those skilled in the relevant art that, because it takes a finite time for any given bottle to travel from the head 34 to the head 36, the procedure described above for first determining the height of the bottle and then adjusting the test limits to allow for this height, must allow for the delay between the receipt of the two signals generated by a single bottle as it passes successively the two heads 34 and 36. Appropriate procedures for allowing for the necessary time delay are well known to those skilled in automated testing procedures.

From the foregoing, it will be seen that the present invention provides a method and apparatus capable of detecting improperly capped bottles having bull nose caps. The present method and apparatus can readily be applied to testing of bottles on commercial high speed production lines without major investment in additional equipment and without disrupting the operation of the line, since the testing can be performed on-line as the bottles traverse the line at their usual speed. Further, since the present method and apparatus can measure the height of the capped bottles, this height measurement can be used to improve the accuracy of other tests conducted on the bottles.

It will be apparent to those skilled in the art that numerous changes and variations can be made in the specific embodiments of the invention described above without departing from the scope of the present invention. For example, the apparatus need not use a single magnetic proximity detector head upstream of the acoustic as illustrated in FIG. 3; the apparatus might include more than one proximity detector head, for example one head offset from the axes of the bottles and one head directly above these axes. Also, the proximity detector head(s) may be downstream or upstream from the acoustic head, with appropriate adjustment being made to the time delays already discussed. The present method need not be practiced in conjunction with the acoustic testing method described above with reference to FIG. 3; instead the present method may be used alone, or in conjunction with other conventional methods for testing capped containers. Accordingly, the foregoing description is to be construed in an illustrative and not in a limiting sense, the scope of the invention being defined by the appended claims.

What I claim is:

1. A method for detecting an improperly applied crown cap on a container, the method comprising:

passing said container bearing said crown cap past a magnetic proximity sensor;

deriving from said sensor a time varying signal representative of the presence and contour of said crown cap and its position on said container; and analyzing said signal to determine whether said time varying signal does or does not correspond to the properties of a predetermined signal expected from a correctly applied crown cap.

2. A method according to claim 1 wherein said analysis of said signal comprises determining whether said signal has one or two maxima.

3. A method according to claim 1 wherein said analysis of said signal comprises determining a merit value for said signal, said merit value being calculated by: (1) determining the areas under the leading end of the signal curve from the initial signal value to the 50% signal value and from the 50% signal value to substantially the initial value on the trailing end of the signal curve and taking the ratio of said areas, said ratio tested against a predetermined value below which represents a reject crown cap and (2) taking the sum of the maxima of the signal and dividing said sum by the minimum signal value intermediate the maxima to determine a second ratio, said second ratio being an indication of a reject crown cap when it less than a second predetermined value.

4. A method according to claim 1 wherein said container has a central axis extending through said crown cap and said magnetic proximity sensor is offset from the plane defined by said axis of said container and the direction of motion of said container as said container passes said magnetic proximity sensor.

5. A method according to claim 1 wherein, before or after passing said magnetic proximity sensor, said container bearing said crown cap is subjected to a process comprising:

inducing vibration in a surface of said container;

detecting sound resulting from said vibration;

deriving information representing the detected sound;

determining whether a frequency component of the information corresponds to a predetermined spectral frequency condition; and determining whether an amplitude component of the information corresponds to a predetermined spectral amplitude condition.

6. A method according to claim 5 further comprising testing the original information representing the detected sound to determine whether a modulating distortion is present therein, and if so compensating for the effects of the modulating distortion, thereby producing demodulated information, determining whether a frequency component of (a) said original information, if no modulating distortion has been found therein, or (b) said demodulated information, if modulating distortion has been found in the original information, corresponds to a predetermined spectral frequency condition; and determining whether an amplitude component of (a) said original information, if no modulating distortion has been found therein, or (b) said demodulated information, if modulating distortion has been found in the original information, corresponds to a predetermined spectral amplitude condition.

7. A method according to claim 5 said signal from said magnetic proximity detector is analyzed to determine the height of said crown cap above a reference surface, and a signal representative of said height is supplied to apparatus used for determining whether a frequency component of the information corresponds to a predetermined spectral frequency condition, and determining whether an amplitude component of the information corresponds to a predetermined spectral amplitude condition, thereby enabling said determinations to allow for variations in said information caused by variations in said height of said crown cap above said reference surface.

8. Apparatus for detecting an improperly applied crown cap on a container, said apparatus comprising:

a magnetic proximity sensor;

transport means for moving said container bearing said cap past said magnetic proximity sensor;

means for deriving from said sensor a time varying signal representative of the presence and contour of said crown cap and its position of said crown cap on said container; and means for analyzing said signal to determine whether said signal does or does not correspond to the properties of a predetermined signal expected from a correctly applied crown cap.

9. Apparatus according to claim 8 wherein said analysis means is arranged to determine whether said signal has one or two maxima.

10. Apparatus according to claim 8 wherein said analysis means is arranged to determine a merit value for said signal by: (1) determining the areas under the leading end of the signal curve from the initial signal value to the 50% signal value and from the 50% signal value to substantially the initial value on the trailing end of the signal curve and taking the ratio of said areas, said ratio tested against a predetermined value below which represents a reject crown cap and (2) taking the sum of the maxima of the signal and dividing said sum by the minimum signal value intermediate the maxima to determine a second ratio, said second ratio being an indication of a reject crown cap when it less than a second predetermined value.

11. Apparatus according to claim 8 for use with a container having a central axis extending through its crown cap, wherein said magnetic proximity sensor and said transport means are arranged so that said magnetic proximity sensor is offset from the plane defined by said axis of said container and the direction of motion of said container as said container passes said magnetic proximity sensor.

12. Apparatus according to claim 8, further comprising:

vibration means for inducing vibration in a surface of said container;

sound detection means for detecting sound resulting from said vibration;

information derivation means for deriving information representing the detected sound; and data processing means arranged to (a) determine whether a frequency component of the information corresponds to a predetermined spectral frequency condition; and (b) determine whether an amplitude component of the information corresponds to a predetermined spectral amplitude condition.

13. Apparatus according to claim 12 wherein said data processing means is further arranged to test the original information representing the detected sound to determine whether a modulating distortion is present therein, and if so to compensate for the effects of the modulating distortion, thereby producing demodulated information, said data processing means further being arranged to carry out the determination of whether a frequency component of (a) said original information, if no modulating distortion has been found therein, or (b) said demodulated information, if modulating distortion has been found in the original information, corresponds to said predetermined spectral frequency condition; and to carry out the determination of whether an amplitude component of (a) said original information, if no modulating distortion has been found therein, or (b) said demodulated information, if modulating distortion has been found in the original information, corresponds to said predetermined spectral amplitude condition.

14. Apparatus according to claim 12 wherein said means for analyzing said signal from said magnetic proximity detector is arranged to determine the height of said crown cap above a reference surface, and to supply a signal representative of said height is said data processing means.

15. Apparatus of claim 8 further including means for detecting when a crown cap is in a predetermined relationship with respect to said magnetic proximity sensor and generating a command to begin acquiring the value of said signal representative of the position of said crown cap on said container.

* * * * *